United States Patent [19]

McEwan

[11] Patent Number: 5,519,400
[45] Date of Patent: May 21, 1996

[54] PHASE CODED, MICRO-POWER IMPULSE RADAR MOTION SENSOR

[75] Inventor: Thomas E. McEwan, Livermore, Calif.

[73] Assignee: The Regents of the University of California, Oakland, Calif.

[21] Appl. No.: 486,171

[22] Filed: Jun. 6, 1995

Related U.S. Application Data

[63] Continuation-in-part of Ser. No. 359,151, Dec. 19, 1994, which is a continuation-in-part of Ser. No. 300,909, Sep. 6, 1994, Pat. No. 5,510,800, which is a continuation-in-part of Ser. No. 44,717, Apr. 12, 1993, Pat. No. 5,361,070.

[51] Int. Cl.⁶ .................................................. G01S 13/58
[52] U.S. Cl. .................................................. 342/28
[58] Field of Search ....................................... 342/22, 28

[56] References Cited

U.S. PATENT DOCUMENTS

| | | | |
|---|---|---|---|
| 5,339,081 | 8/1994 | Jefferis et al. | 342/28 |
| 5,361,070 | 11/1994 | McEwan | 342/21 |
| 5,432,516 | 7/1995 | Cherry et al. | 342/28 |
| 5,457,394 | 10/1995 | McEwan | 342/22 X |
| 5,465,094 | 11/1995 | McEwan | 342/28 |

*Primary Examiner*—John B. Sotomayor
*Attorney, Agent, or Firm*—Henry P. Sartorio

[57] ABSTRACT

A motion sensing, micro-power impulse radar MIR impresses on the transmitted signal, or the received pulse timing signal, one or more frequencies lower than the pulse repetition frequency, that become intermediate frequencies in a "IF homodyne" receiver. Thus, many advantages of classical RF receivers can be thereby be realized with ultra-wide band radar. The sensor includes a transmitter which transmits a sequence of electromagnetic pulses in response to a transmit timing signal at a nominal pulse repetition frequency. A receiver samples echoes of the sequence of electromagnetic pulses from objects within the field with controlled timing, in response to a receive timing signal, and generates a sample signal in response to the samples. A timing circuit supplies the transmit timing signal to the transmitter and supplies the receive timing signal to the receiver. The relative timing of the transmit timing signal and the receive timing signal is modulated between a first relative delay and a second relative delay at an intermediate frequency, causing the receiver to sample the echoes such that the time between transmissions of pulses in the sequence and samples by the receiver is modulated at the intermediate frequency. Modulation may be executed by modulating the pulse repetition frequency which drives the transmitter, by modulating the delay circuitry which controls the relative timing of the sample strobe, or by modulating amplitude of the transmitted pulses. The electromagnetic pulses will have a nominal center frequency related to pulse width, and the first relative delay and the second relative delay between which the timing signals are modulated, differ by less than the nominal pulse width, and preferably by about one-quarter wavelength at the nominal center frequency of the transmitted pulses.

30 Claims, 4 Drawing Sheets

5,519,400

PHASE CODED, MICRO-POWER IMPULSE RADAR MOTION SENSOR

The United States government has rights in this invention pursuant to Contract Number W-7405-ENG-48 between the United States Department of Energy and the University of California for the operation of Lawrence Livermore National Laboratory.

CONTINUING APPLICATION DATA

The present application is a continuation-in-part of prior U.S. patent application entitled SHORT RANGE, ULTRA-WIDE BAND RADAR WITH HIGH SOLUTION SWEPT RANGE GATE, filed Dec. 19, 1994, Application No. 08/359,151, still pending, which is incorporated by reference as if fully set forth herein; which in turn is a continuation-in-part of Application No. 08/300,909, filed Sep. 6, 1994; now U.S. Pat. No. 5,510,800 which in turn is a continuation-in-part of Application No. 08/044,717, filed Apr. 12, 1993, now U.S. Pat. No. 5,361,070, issued Nov. 1, 1994.

BACKGROUND OF THE INVENTION

1. Field of the Invention

The present invention relates generally to an improved ultra-wide band micro-power impulse radar sensor, for detecting motion or other characteristics of objects within a range gated field.

2. Description of Related Art

Prior art motion sensors have been primarily based on ultra sound, passive infrared sensors, and so-called FM-CW radar sensors. Also, some Doppler radar systems have been used for motion detection in prior art. All of these prior art systems suffer a number of limitations that make them impractical for a large number of uses.

As described in U.S. Pat. No. 5,361,070, of which the present application is a continuation-in-part, an ultra-wide band radar motion sensor overcomes many of the disadvantages of these prior art systems.

However, radars that employ extremely wide RF bandwidths generally use wide band oscilloscopes or sampling circuits as direct conversion receivers since the use of intermediate frequencies (IF) is precluded by the large bandwidths involved. For instance, receivers for the wide band radar motion sensors have been based on amplification at base band or close to DC, resulting in high noise levels due to the 1/f noise in virtually all electronic devices. Also, high gain at a single frequency frequently leads to oscillations due to input/output signal feedback. Additional problems include: 1) problems with jamming signals, which are indistinguishable from authentic radar returns and may result in false alarms; 2) high level impulse noise sources weigh heavily on the averaging process in the receiver, because such impulses cannot be easily clipped in amplitude; 3) the receiver relies on simple Gaussian averaging for selectivity and for rejection of interference, which can lead to false triggering at high jamming levels; 4) there is no received "carrier" to operate an automatic gain control circuit for more consistent performance and wider dynamic range; 5) there is no means to encode transmissions for selective reception in co-located systems; 6) and there is no way to deduce the direction of movement, or to deconvolve the pseudo-Doppler returns in the magnitude and phase components for signal processing. Accordingly, it is desirable to improve the wide band radar motion sensor to address the issues related above.

SUMMARY OF THE INVENTION

The present invention overcomes the limitations of the ultra-wide band systems, to provide a new class of motion sensing, micro-power, ultra-wide band radars, by impressing on the transmitted signal, or on the receive pulse timing signal, one or more frequencies lower than the pulse repetition frequency that become intermediate frequencies in a "IF homodyne" receiver. Thus, many advantages of the classical RF receivers can be realized in the ultra-wide band radar including:

1) receiver gain is distributed at several frequencies to eliminate feedback effects and 1/f noise, 2) automatic gain control circuits can be implemented, 3) a wide band IF noise limiter can be used to substantially reduce interference, 4) a statistical detector can be used to convert receive sample averaging statistics from Gaussian to Bernoulli for graceful sensitivity degradation in the presence of jamming while completely eliminating the possibility of false alarms due to jamming, 5) the IF signal impressed on the transmitted signal may be a coded sequence to allow selective operation of multiple co-located sensors;

6) RF quadrature phase coding can be transmitted for direction sensing and vector processing (magnitude and phase, or complex FFT variables) of sub-$\lambda$ pseudo-Doppler radar returns.

Accordingly, the present invention can be characterized as an apparatus for detecting a characteristic of objects within a field, comprising a transmitter which transmits a sequence of electro-magnetic pulses (or alternatively short bursts) in response to a transmit timing signal at a nominal pulse repetition frequency. A receiver samples echoes of the sequence of electro-magnetic pulses from objects within the field with controlled timing, in response to a receive timing signal, and generates a sample signal in response to the samples. The sample signal indicates a characteristic, such as motion, of objects within the field. A timing circuit supplies the transmit timing signal to the transmitter and supplies the receive timing signal to the receiver. The relative timing of the transmit timing signal and the receive timing signal is modulated between a first relative delay and a second relative delay at an intermediate frequency, causing the receiver to sample the echoes such that the time between transmissions of pulses in the sequence and samples at the receiver is modulated at the intermediate frequency. Modulation may be executed by modulating the pulse repetition frequency which drives the transmitter, or, optionally, by modulating the delay circuitry which controls the relative timing of the sample strobe. Also, pulse amplitude modulation may be used.

The electro-magnetic pulses will have a nominal center frequency and pulse width, and the first relative delay and the second relative delay between which the timing signals are modulated, differ by less than the nominal pulse width, and preferably by about one-quarter wavelength at the nominal center frequency of the transmitted pulses.

According to another aspect of the invention, the timing circuit modulates the relative timing of the transmit timing signal and the receive timing signal at a first intermediate and a second intermediate frequency (which may be lower than the first in some embodiments). For instance, two modulation signals can be combined such as by an exclusive-OR operation and the combination used to modulate the transmit timing. In this aspect, the receiver includes a first intermediate frequency stage, followed by a second intermediate frequency stage. The first intermediate frequency stage includes an intermediate frequency amplifier, and a synchronous detector which is synchronous with the first intermediate frequency modulation. Automatic gain control can be implemented in the intermediate frequency stage. In addition, a second intermediate frequency stage is coupled to the output of the first intermediate frequency stage. The second intermediate frequency stage includes a second intermediate frequency amplifier and a synchronous detector which is synchronous with the second intermediate frequency modulation of the relative timing between the transmit timing signal and the receive timing signal. The output of the second intermediate frequency stage is supplied to an amplitude or peak detector, which generates an output indicating motion in the field.

The synchronous detector in the first intermediate frequency stage provides an intermediate frequency noise limiter, and in the second intermediate frequency stage provides a statistical detector which translates the Gaussian profile of the received signal to a Bernoulli profile, greatly improving jammer tolerance.

According to yet another aspect of the invention, the relative timing is modulated only at an intermediate frequency. The receiver includes an intermediate frequency amplifier which supplies its output to a switch circuit. The switch circuit is controlled synchronously with the modulation of the relative timing of the transmit timing signal and the receive timing signal, and supplies the output of the intermediate frequency amplifier to a first output and a second output. The first and second outputs provide an in-phase signal and a quadrature phase signal at the receiver. These signals can be used for vector processing or fast Fourier transform (FFT) processing of the received image from the field, so that speed and direction of motion can be determined or other information can be developed.

According to yet another aspect of the invention, the timing circuit modulates the relative timing between the transmit timing signal and the receive timing signal, according to a coded intermediate frequency modulation signal. By providing co-located (or nearby) sensors with different codes driving the modulation circuitry, interference from adjacent sensors is avoided.

In sum, a phase-coded, double conversion, homodyne ultra-wide band radar motion sensor with a statistical detector has been provided based on the transmission and detection of micro-power impulse radar signals. These features may be implemented in various combinations to provide an improved ultra-wide band radar system to detect a variety of characteristics of objects within a controlled range field. Further, the system uses very low power and low cost components, making it within reach of a wide variety of commercial applications. Current possibilities for such commercial uses include robotic and security system sensors, automotive radar, medical applications for organ motion sensing and the like, and, generally, all applications of range gated proximity sensors where the features of channel coding, graceful sensitivity degradation in the presence of noise and jamming, and direction sensing or general quadrature signature processing are desirable.

Other aspects and advantages of the present invention can be seen upon review of the figures. A detailed description and claims follow.

DETAILED DESCRIPTION OF PREFERRED EMBODIMENTS

Figure 1:
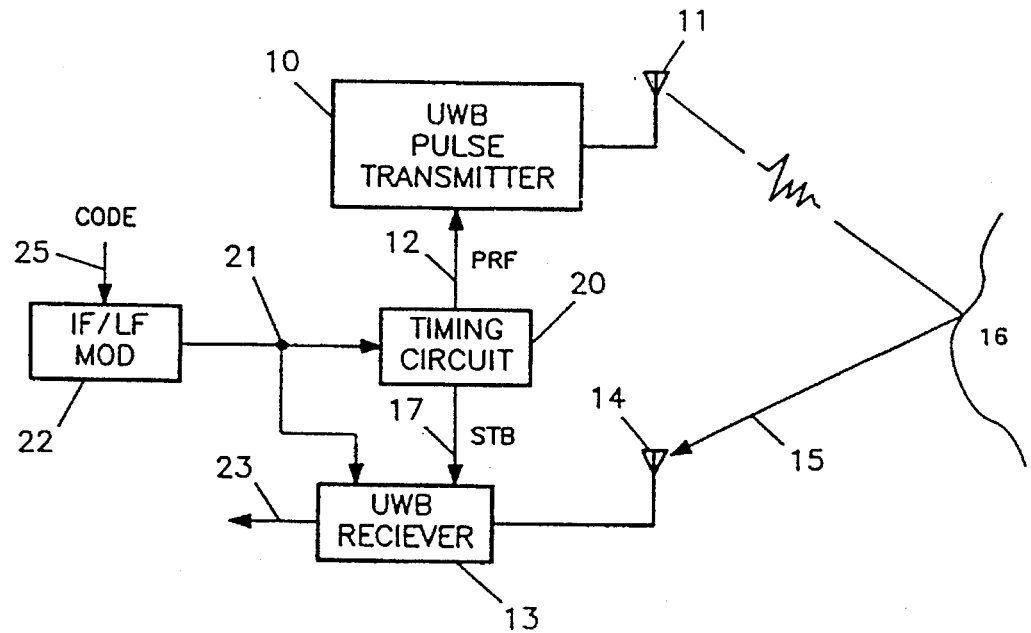
FIG. 1 is a conceptual block diagram of the improved ultra-wide band radar sensor according to the present invention.
Figure 2:
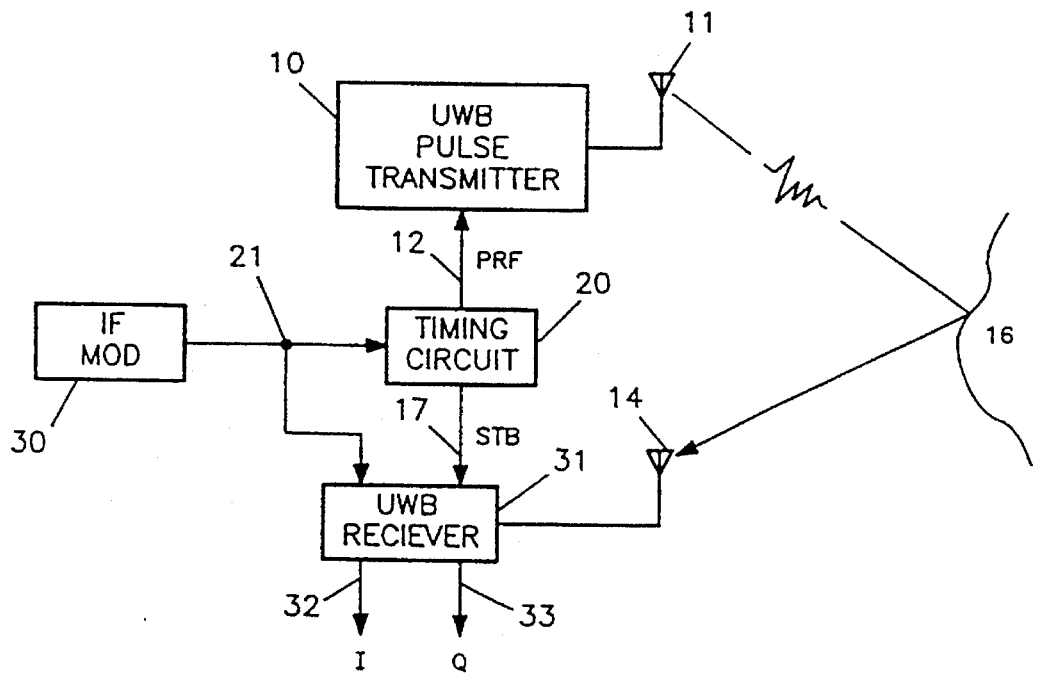
FIG. 2 is a conceptual diagram of an alternative embodiment of the ultra-wide band radar sensor according to the present invention.

A detailed description of embodiments of the present invention is provided with respect to the figures, in which FIGS. 1 and 2 conceptually illustrate the sensor according to the present invention.

FIG. 1 shows a sensor according to the present invention which includes an electro-magnetic pulse transmitter 10, having an antenna 11 which emits an ultra-wide band pulse at a radio frequency such as 2 to 10 GHz, or a short burst of radio frequency energy for narrower band width operation, in response to a transmit timing signal on line 12. The transmit timing signal on line 12 defines the pulse repetition frequency PRF for the transmitter 10. Thus, for instance, the transmitter will emit short pulses or bursts of RF energy at a rate of about 2 MHz in one example with a duty cycle of about 0.1% to about 0.5%.

A wide band receiver 13 including antenna 14 receives echoes, generally represented by the arrow 15, off of objects 16 within range of the sensor. The receiver 13 includes a sampler which is strobed by a receive timing signal on line 17. The receive timing signal constitutes a strobe signal STB which is generated such that the relative timing of the transmit timing signal on line 12 and the receive timing signal on line 17 define a range for the sensor. Thus, the strobe signal on line 17 is delayed relative to each pulse of the pulse repetition frequency signal on line 12 by an amount equal to about the round trip time of flight of an electromagnetic pulse for an object within the range. The range according to preferred implementations of the present invention may vary from 100 feet or greater down to less than a foot. Also, it may be dynamically swept over a field of ranges.

According to the present invention, the receive timing signal on line 17 and the transmit timing signal on line 12 are generated by a timing circuit 20, which modulates the relative timing of the transmit timing signal and the receive timing signal between a first relative delay and a second relative delay in response to a modulation signal on line 21. The difference between the first and second relative delays is less than the nominal pulse width, and preferably about one-quarter wavelength at the nominal center frequency of the pulse. The modulation signal on line 21 is generated by a combined intermediate frequency IF and low frequency LF modulation circuit 22 for the embodiment of FIG. 1. The low frequency modulation circuit 22 may be a second intermediate frequency which is not lower than the first intermediate frequency in some embodiments. Thus, the relative delay between the transmit timing signal on line 12 and the receive timing signal on line 17 is modulated between a first relative delay, and a second relative delay at a first intermediate frequency and at a second intermediate frequency in response to the modulation signal on line 21. An alternative approach to modulation would involve modulating the transmit pulse amplitude, rather than the transmit delay. Similar receiver effects can be achieved.

Modulation introduces the intermediate and low frequency signals into the echoes sampled by the receiver 13. The receiver 13 also includes circuitry which is synchronous with the modulation signal on line 21, and produces an output signal on line 23 indicating motion or other characteristics of the object 16 in the field. Thus, advantages of classic RF receivers can be realized using first intermediate frequency and the second intermediate frequency stages in the receiver 13.

FIG. 1 also illustrates coding of the modulation signal to prevent interference between closely positioned or "co-located" sensors. Thus, the code signal on line 25 imposes a coded sequence on the modulation signal on line 21, which is intended to be different than coded sequences in the other sensors nearby.

FIG. 2 illustrates an alternative implementation of the sensor of the present invention. Elements in the system of FIG. 2 have been given the same reference numbers as corresponding parts in FIG. 1 for simplicity. The key difference between the system of FIG. 1 and the system of FIG. 2 is found in the modulation circuit 30 and in the receiver 31. Modulation circuit in FIG. 2 modulates the timing circuit 20 at only intermediate frequency. The receiver 31 includes circuitry which is synchronous with the intermediate frequency to produce the outputs.

Also, the receiver 31 is adapted to provide in-phase I and quadrature Q outputs 32 and 33, respectively. These outputs can be used to provide pseudo-Doppler radar returns, allowing direction sensing and vector processing. According to this aspect, the relative timing between the pulse repetition frequency on line 12 and the strobe signal on line 17 is modulated between a first relative delay and a second relative delay which differ by about one-quarter wavelength at the nominal center frequency of the transmitted pulses.

Figure 3:
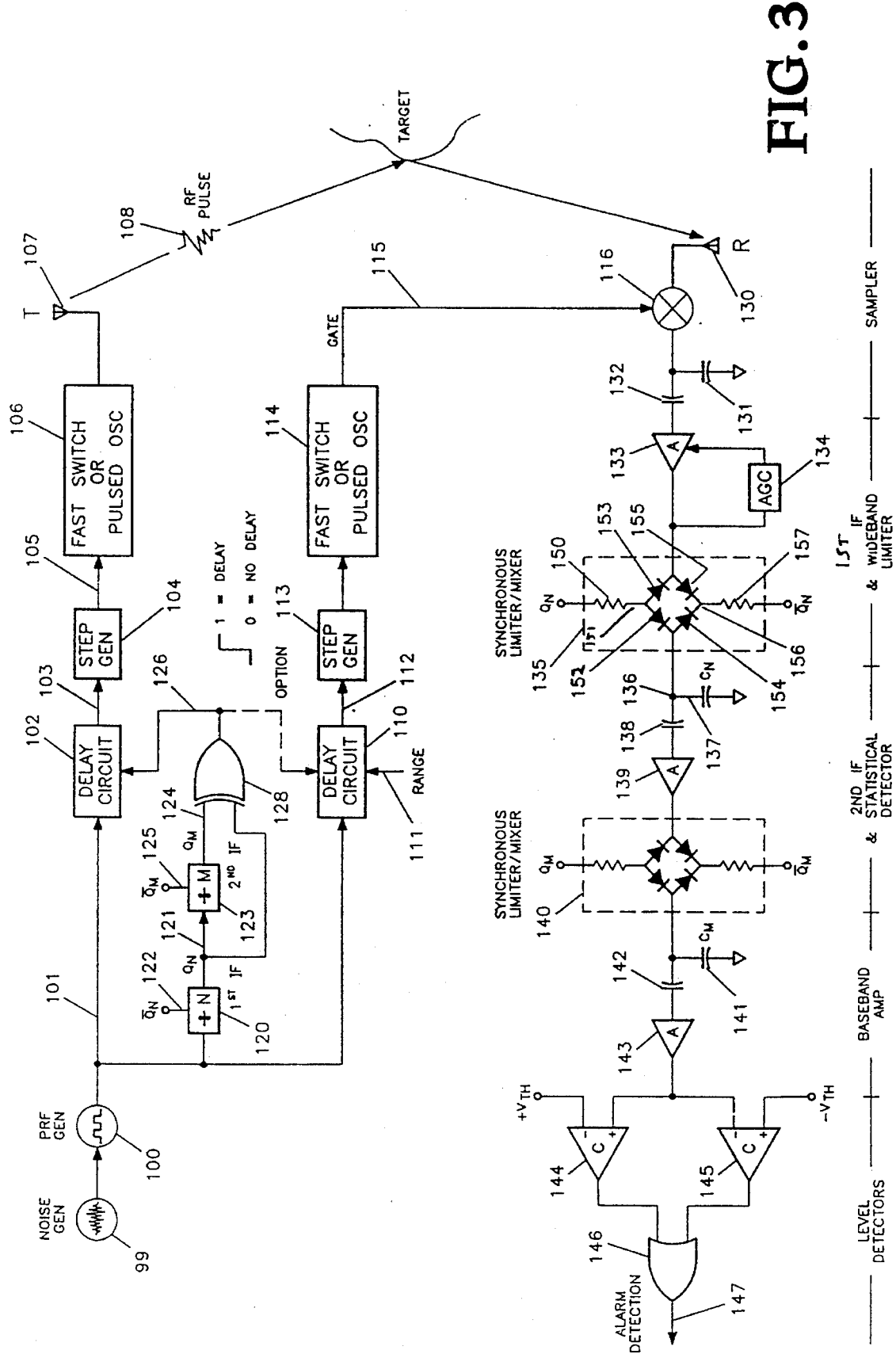
FIG. 3 is a schematic block diagram illustrating functional blocks in the sensor of FIG. 1.

FIG. 3 provides a more detailed block diagram of the sensor of FIG. 1. Thus, as can be seen in FIG. 3, the timing circuit includes a PRF generator 100 operating at about 2 MHz. The pulse repetition frequency generator 100 is dithered by a random noise signal generator 99 in the preferred system to improve immunity to nearby systems. A random dithering of the pulse repetition frequency makes it extremely unlikely that a given system will generate pulses at precisely the same time as a nearby system.

The output of the PRF generator 100 is supplied on line 101 to a transmit delay circuit 102. The output of the transmit delay circuit is supplied on line 103. Line 103 is connected to the transmitter which includes a step generator 104. The step generator 104 supplies a signal on line 105 which drives a fast switch or pulsed oscillator 106. The fast switch or pulsed oscillator 106 is coupled to an antenna 107 which transmits the RF pulse 108 (or short multi-cycle bursts in alternative systems).

The timing circuit also includes a receive delay circuit 110 which is connected to line 101. The receive delay circuit 110 has an adjustable delay range which is controlled by the input 111. The output of the receive delay circuit 110 is supplied to the receiver across line 112. The receiver includes a step generator 113 and a fast switch or pulsed oscillator 114 which generates a gate signal on line 115 for a sampler 116.

The timing circuit also includes modulation circuitry. Modulation circuitry in the embodiment of FIG. 3 includes a first divider 120 which divides the signal on line 101 by an integer N and produces the output signal $Q_N$ on line 121, and the complement of that signal on line 122. The signal $Q_N$ is connected as input to a second divider 123 which divides the signal on line 121 by an integer M and generates the output $Q_M$ on line 124 and the complement of that signal on line 125. The signal on line 121 and the signal on line 124 are connected to an exclusive-OR gate 128 which provides a modulation signal on line 126 to the delay circuit 102 in the transmit path in the embodiment shown in FIG. 3. Optionally, this modulation signal can be applied to the delay circuit 110 in the receive path.

The modulation of the delay circuit 102 results in modulation of the transmit timing signal on line 103 by an amount equal to nominally one-quarter wavelength of the center frequency of the RF pulse 108, or by an amount less than the pulse width of the signal 108 such that the sample gate is opened during an interval to sample the round trip echo for both relative delays. The amount of modulation, that is the timing shift on the transmit timing signal, may be arbitrarily long or short; but the preferred timing shift is one-quarter wavelength.

This results in imposing the first and second intermediate frequencies as represented by the signals at $Q_N$ and $Q_M$ on the signal sampled by the receiver.

The receiver circuitry includes an antenna 130 coupled to the sampler 116. The sampler 116 is strobed by the signal on line 115, and coupled to a charge holding capacitor 131. The charge holding capacitor is AC coupled through capacitor 132 to the input of an intermediate frequency amplifier 133. An automatic gain control circuit 134 is coupled to the intermediate frequency amplifier 133. The output of the intermediate frequency amplifier 133 is connected to a synchronous detector 135, which may also be called a synchronous rectifier, limiter, or mixer. The synchronous detector 135 is synchronized with the first intermediate frequency signal $Q_N$ and produces an output on line 136. The output on line 136 is applied to a capacitor 137 which holds the signal at the second intermediate frequency. This capacitor is AC coupled through capacitor 138 to a second intermediate frequency amplifier 139. The output of the second intermediate frequency amplifier 139 is connected to a synchronous detector 140 which is synchronized with the second intermediate frequency signal $Q_M$, as shown. Again, the output of the synchronous detector 140 is connected to a capacitor 141 which holds the broadband signal, which is AC coupled through capacitor 142 to an amplifier 143. Amplifier 143 is connected to the input of a threshold detector which is based on a first comparator 144 having the output of the amplifier 143 connected to its positive input, and a threshold voltage of $+V_{TH}$ connected to its negative input. Also, a comparator 145 is included having its negative input connected to the output of the amplifier 143 and its positive input coupled to a negative threshold $-V_{TH}$. The outputs of the comparators 144 and 145 are connected to an OR gate 146. The output of the OR gate 146 is supplied on line 147, indicating motion detection. This signal might be used to drive an alarm or other signal processing.

The synchronous detectors 140 and 135 have similar structures. Thus, detector 135 will be described here as representative. It includes a resistor 150 connected between the signal $Q_N$, and node 151. Node 151 is connected to the anodes of diodes 152 and 153. The cathodes of diodes 152 and 153 are connected to line 136 and the output of the amplifier 133, respectively. Also, the anodes of diodes 154 and 155 are connected to line 136 and the output of amplifier 133, respectively. The cathodes of diodes 154 and 155 are connected to node 156. Resistor 157 is connected between node 156 and the signal $\overline{Q_N}$.

The synchronous detector 135 provides a wide band limiter for the intermediate frequency amplifier such that high spikes of noise or interference are limited. The synchronous detector 140 provides a statistical detector for the second intermediate frequency amplifier section translating the noise characteristics from a Gaussian to a Bernoulli profile. This greatly improves the jammer tolerance of the system. Thus, as can be seen in FIG. 3, the receive path includes a sampler which is responsive to the gate signal on line 115 to sample the echoes of transmitted pulses. The output of the sampler is applied to a first intermediate frequency stage including a wide band limiter. A first stage is coupled to a second intermediate frequency stage which includes a statistical detector. The output of the statistical detector is applied to a base band amplifier, which drives a level detector which provides an output of the system.

According to one embodiment, the PRF generator 100 operates at about 2 MHz, and drives the transmit path through the transmit delay circuit and drives a gate path through a range delay circuit. The transmit delay circuit is modulated by the XOR gated combination of a first intermediate frequency which is equal to PRF/N or about 10 KHz in one example, and a second intermediate frequency which is equal to PRF/(N*M) which is about 300 Hz in one example. Thus, the transmitted RF pulse is toggled between two different delays at two different frequencies. The sampler in the receiver samples at the pulse repetition frequency, but the charge holding capacitor 131 is sufficiently large that it cannot follow the PRF but does follow changes at the first and second intermediate frequencies. The signal through the first intermediate frequency stage is essentially at the first intermediate frequency with side bands at the second intermediate frequency and its multiples. The first synchronous rectifier toggles at the first intermediate frequency, placing a residual at the second intermediate frequency on the holding capacitor 137 for amplification by the second intermediate frequency stage. The second synchronous rectifier 140 toggles at the second intermediate frequency, so that the frequencies on capacitor 141 are now at base band, representing the "Doppler" signature of a moving target. This base band signal is further amplified where necessary and applied to the plus and minus level detectors, having outputs combined to activate an alarm when the Doppler signature is strong enough. For instance, if a sufficiently large target moves through the range gate, then the signature will be strong enough to trip the detector.

The synchronous detectors 135 and 140 also form limiters. In the first intermediate frequency stage, if a noise spike is present, it can only charge the capacitor 137 at a slow rate, thereby minimizing its effect. It is similar to the wide band IF noise limiters that are common in communications receivers, or Dicke-Fix limiters in radar receivers. The limiter in the second intermediate frequency stage has another purpose: large, slower fluctuations due to jamming are voltage slew-rate limited such that most valid Doppler signatures are unaffected, but large fluctuations due to high level jamming are limited. In practice, the circuit is enclosed in a feedback loop that locks on the average signal level and the slightest change becomes slew-rate limited. This has the exact effect in the signal averaging process of converting Gaussian statistics to Bernoulli statistics. Thus, each swing of the second intermediate frequency signal is treated as a flip of a coin. In the Gaussian process, one thousand samples has a standard deviation $\sigma$ equal to 31.6, whereas in the Bernoulli process one thousand coin flips has a standard deviation $\sigma$ equal to 15.8. It is possible to set the thresholds $+V_{TH}$ and $-V_{TH}$ such that any amount of jamming will not exceed the threshold. Thus, the system becomes jam proof. At high levels of jamming, sensitivity is reduced by the clipping action of the limiters, which clip both signal and jamming. Thus, the system gracefully degrades in sensitivity in the presence of increased jamming.

Figure 4:
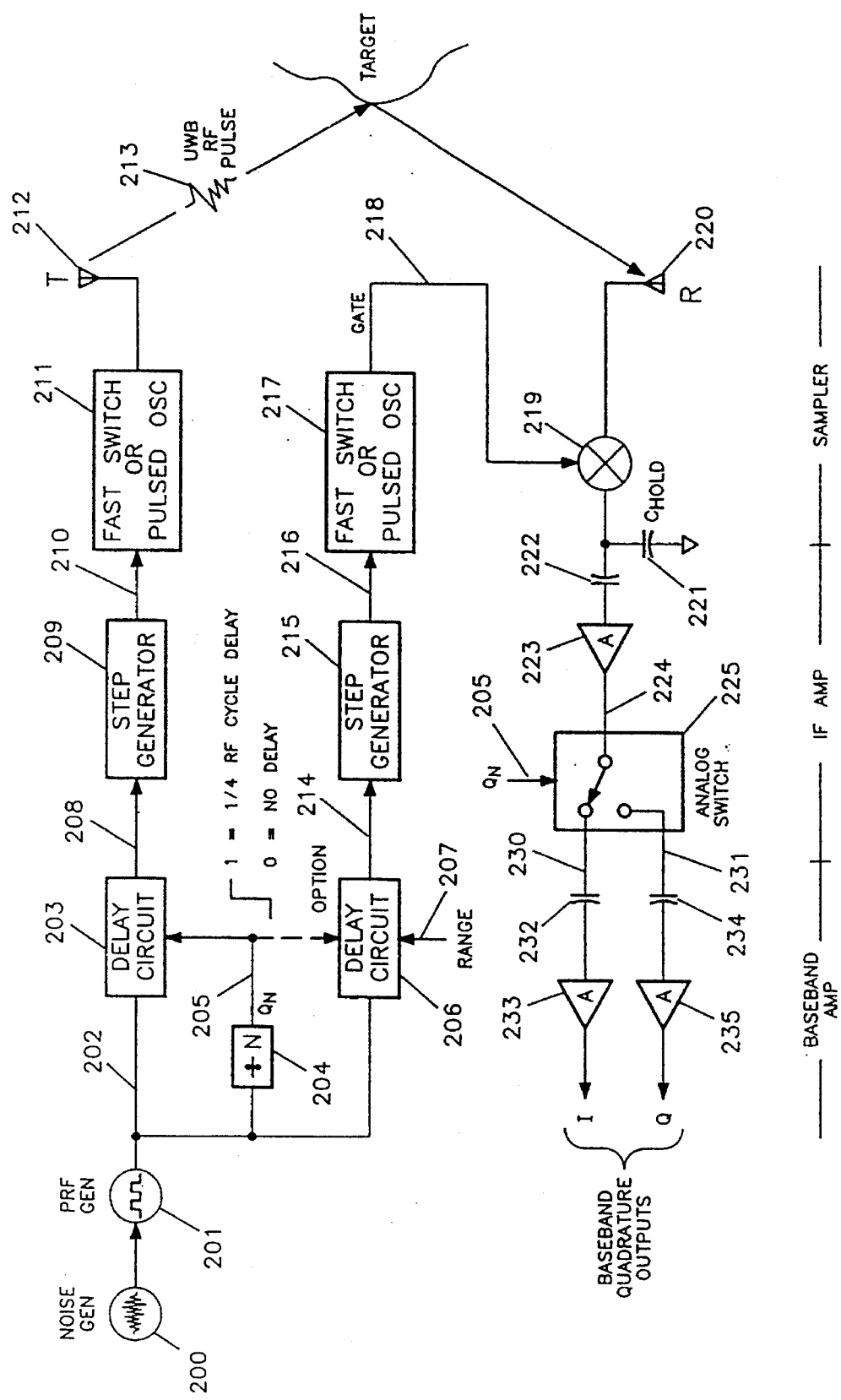
FIG. 4 is a schematic block diagram illustrating functional blocks in the sensor of FIG. 2.

FIG. 4 is a block diagram showing the functional blocks of the sensor shown in FIG. 2. In FIG. 4, the system includes a noise dithering source 200 which controls a pulse repetition frequency PRF generator 201. The PRF generator 201 supplies an output on line 202 to a transmit delay circuit 203. It also drives a divider 204 which supplies a modulation signal $Q_N$ on line 205. Similarly, the signal on line 202 drives a receive delay circuit 206, which has a delay which defines the range of the sensor as described above, as set by the signal on line 207.

The output of the transmit delay circuit on line 208 drives a step generator 209. The output of the step generator 209 on line 210 drives the fast switch or pulsed oscillator 211. The fast switch or pulsed oscillator 211 is coupled to an antenna 212 which supplies the RF pulse 213 or short multi-cycle burst.

The receive delay circuit 206 supplies a receive timing signal on line 214 to a step generator 215. The step generator 215 supplies a signal on line 216 which drives a fast switch or pulsed oscillator 217. The output of the fast switch or pulsed oscillator 217 provides a gate signal on line 218 to sampler 219. Sampler 219 is coupled to the antenna 220, and samples the received echoes in response to the gate signal on line 218. The output of the sampler is dumped into a charge holding capacitor 221. The output of the charge holding capacitor 221 is AC coupled through capacitor 222 to an intermediate frequency amplifier 223. The output of the amplifier 223 is supplied on line 224 to an analog switch 225. The analog switch 225 is controlled by the modulation signal $Q_N$ on line 205 to supply the signal on line 224 to a first output on line 230 or second output on line 231 synchronously. The signal on line 230 is AC coupled through capacitor 232 to amplifier 233. The output of the amplifier 233 is the "I" or in-phase output for the system. The signal on line 231 is AC coupled through capacitor 234 to amplifier 235 which supplies the "Q" output of the base band quadrature set.

This system is similar to that described above with respect to FIG. 3 in the transmit and gating path. However, only a single intermediate frequency of about 10 KHz in this example is used. The transmit delay circuit toggles between two values corresponding in time to one-quarter of an RF cycle, or about 125 picoseconds at a nominal 2 GHz center frequency. The receive path gating is unmodulated and defines the detection range. The value of the charge holding capacitor 221 in the receive sampler is large enough that it cannot follow voltage variations at the pulse repetition frequency, but can follow variations at the intermediate frequency. These variations are amplified and demultiplexed into two channels, which represent Doppler returns that have a 90° phase relationship, the so-called in-phase "I" and quadrature "Q" outputs. These outputs can be processed by well known vector techniques to determine motion direction, and Doppler magnitude and phase where the net motion magnitude is equal to $(I^2+Q^2)^{1/2}$. Magnitude and phase are of particular importance for imaging systems, such as stud finders and heart monitors, that emit sinusoidal bursts and yet need a linear net motion response.

Figure 5:
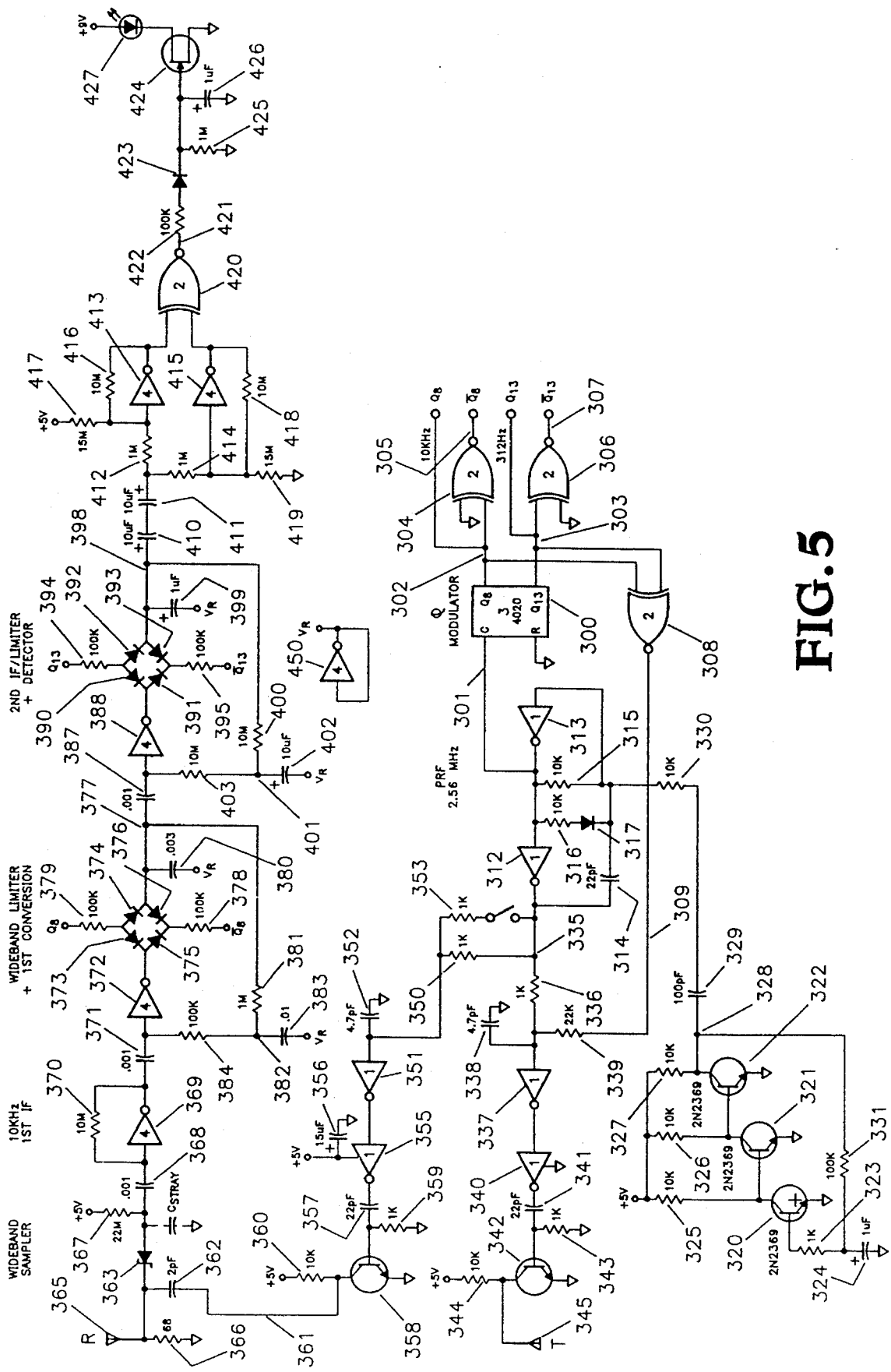
FIG. 5 is an electrical schematic diagram of one embodiment of the ultra-wide band sensor implemented according to the architecture of FIG. 3.

FIG. 5 is a detailed electrical schematic diagram of a sensor having the architecture shown in FIG. 3. This schematic diagram is meant to be representative of one implementation of the present invention, and the values for the components provided in the drawing are representative of this one embodiment.

The system includes the delay modulator circuit which is based on a counter 300. The counter 300 is clocked at the pulse repetition frequency across line 301 and produces signals at the Q8 and Q13 outputs on lines 302 and 303, respectively. The signal on line 302 is inverted by the exclusive-OR gate 304 to generate Q8 on line 305. The signal on line 303 is inverted by exclusive-OR gate 306 to produce Q13 on line 307. The signals Q8 and Q13 on lines 302 and 303 are supplied through an exclusive-OR gate 308 to provide the modulation signal on line 309.

The pulse repetition frequency is generated by the series inverters 312 and 313 where the output of inverter 312 is connected through capacitor 314 to the input of inverter 313. The output of inverter 313 is connected to the input of inverter 312, and to the input of inverter 313 across resistor 316 and diode 317 connected in series. Resistor 315 is also connected to the feedback path from the output of inverter 313 to its input. The pulse repetition frequency on line 301 is about 2.56 MHz in this embodiment.

The pulse repetition frequency is dithered by a noise source composed of the bipolar transistors 320, 321, and 322. The base of transistor 320 is connected through resistor 323 to capacitor 324, which is coupled to ground. The emitter of transistor 320 is connected to ground. The collector of transistor 320 is connected through resistor 325 to the 5 volt supply. Transistor 321 has its base connected to the collector of transistor 320, its collector connected across resistor 326 to the 5 volt supply, and its emitter connected to ground. Similarly, transistor 322 has its base connected to the collector of transistor 321, its collector connected to resistor 327 to the 5 volt supply, and its emitter connected to ground. A feedback resistor 331 is connected from the capacitor 324 to the collector of transistor 322. The collector of transistor 322 is a noise dither signal on line 328 which is connected through capacitor 329 and resistor 330 to the input of inverter 313 of the PRF oscillator.

The noise dithered pulse repetition frequency signal on line 335 is split into the transmit timing signal path and the receive timing signal path. The transmit timing signal path is coupled across resistor 336 to the input of inverter 337. Also, capacitor 338 is connected from the input of inverter 337 to ground. Resistor 339 is connected from the input of inverter 337 to the output of the exclusive-OR gate 308 to receive the modulation signal on line 309, such that the delay generated at the output of inverter 337 is modulated by the modulation signal. The output of the inverter 337 is connected to the input of inverter 340. The output of inverter 340 is connected through capacitor 341 to the base of transistor 342. A resistor 343 is connected from the base of transistor 342 to ground. The collector of transistor 342 is connected across resistor 344 to the 5 volt supply. The emitter of transistor 342 is connected to ground. Also, the collector of transistor 342 is connected to the transmit antenna 345. Thus, pulses of RF energy are generated by the transistor 342 in response to the pulse repetition frequency signal, modulated by the modulation signal on line 309.

In the receive path, the signal on line 335 is connected through resistor 350 to the input of inverter 351. Also, capacitor 352 is connected from the input of inverter 351 to ground. A parallel resistor 353 coupled across resistor 351 can be switched in or out to alter the range gate positions.

The output of inverter 351 is connected to the input of inverter 355. The inverter 355 is coupled to the 5 volt supply, and a bypass capacitor 356 is connected between the supply and ground.

The output of the inverter 355 is connected through a capacitor 357 to the base of transistor 358. Also, resistor 359 is connected from the base of transistor 358 to ground. The emitter of transistor 358 is connected to ground, and the collector of transistor of 358 is connected through resistor 360 to the 5 volt supply. Also, the collector of transistor 358 supplies the strobe signal on line 361. The strobe signal is supplied across capacitor 362 to the cathode of the diode 363. Schottky diode 363 provides a sampling function for the receiver. Thus, the cathode of diode 363 is also coupled to the receive antenna 365. A resistor 366 is coupled from the cathode of diode 363 to ground. The anode of diode 363 is coupled across resistor 367 to the 5 volt supply. A stray capacitance, represented by the capacitor $C_{STRAY}$ shown in the figure, provides a charge holding function for the circuit. Thus, the anode of diode 363 is coupled across the charge holding capacitor $C_{SPRAY}$ to ground. A capacitor 368 provides AC coupling to the input of inverter 369. Resistor 370 is coupled across the output and input of inverter 369 to feedback. The output of the inverter 369 is coupled across capacitor 371 to the input of inverter 372. The output of inverter 372 is connected to the input of the synchronous rectifier which is composed of diodes 373, 374, 375, and 376. Thus, the output of the inverter 372 is connected to the cathode of diode 373 and the anode of diode 375. The anode of diode 373 is connected across resistor 379 to the signal Q8. The cathode of diode 374 and the anode of diode 376 are connected to the output terminal 377. The cathode of diode 376 and the cathode of diode 375 are coupled together and across resistor 378 to the signal $\overline{Q8}$. A capacitor 380 is coupled from line 377 to the reference potential $V_r$. Also, a feedback resistor 381 is connected from line 377 to node 382. Node 382 is connected across capacitor 383 to the reference voltage $V_r$, and across resistor 384 to the input of amplifier 372.

The output of the synchronous rectifier on line 377 is connected through capacitor 387 to the input of inverter 388. The output of inverter 388 drives the synchronous rectifier made up of diodes 390, 391, 392, and 393, and of resistors 394 and 395. These components are connected in the same manner as the synchronous rectifier composed of diodes 373, 374, 375, and 376. However, this synchronous detector is driven by the signal Q13 and $\overline{Q13}$. The output node of the synchronous rectifier on line 398 is coupled across capacitor 399 to a reference potential $V_r$. Also, the signal on line 398 is coupled across a feedback resistor 400 to node 401. Node 401 is coupled across capacitor 402 to the reference potential $V_r$, and across resistor 403 to the input of amplifier 388.

The $V_r$ is generated by a feedback arrangement based on inverter 450, which has its output and input coupled together as is shown in the figure. The inverters 369, 372, 388, 413, 415, and 450 are implemented with Motorola MC14069UB. The inverters 312, 313, 337, 340, 351 and 355 are implemented with National 74HC04 The XOR gates 304, 306, 308, and 420 are implemented with Motorola MC14077. The counter 300 is a Motorola MC14020. The bipolar transistors 342 and 358 are Motorola BFR92. The Schottky diode 363 is a Hewlett Packard HSMS2810. The other diodes in the figure are Texas Instruments IN4148. The supply voltages are generated using a battery circuit such as is well known in the art, such as a National LM78L05 regulator.

The output of the synchronous rectifier at the second intermediate frequency defined by Q13 is supplied on line 398 through series capacitors 410 and 411 to the level detector by means of a first resistor 412 connected to the input of inverter 413 and the second resistor 414 connected to the input of inverter 415. The output of inverter 413 is connected across resistor 416 to the input of inverter 413. Also, the input is connected across resistor 417 to the 5 volt supply. The output of inverter 415 is connected across resistor 418 to the input of inverter 415. Also, the input of inverter 415 is connected across resistor 419 to ground. The outputs of inverters 413 and 415 are also coupled through exclusive-OR gate 420 to provide a signal on line 421. The signal on line 421 is connected through resistor 422 and diode 423 to the gate of transistor 424. Also, a resistor 425 and a capacitor 426 are coupled in parallel from the gate of transistor 424 to ground. The source of transistor 424 is connected to ground. The drain of transistor 424 drives an LED 425 which is coupled to a high positive potential through an external alarm load or current limiting resistor.

Accordingly, an improved micro-power impulse radar (MIR) motion sensor is provided, which is capable of realizing the advantages of classic RF receivers which use intermediate frequency amplifiers. Further, the system can be adapted to provide quadrature outputs allowing speed and direction processing for motion in the field of the system. Also, the system is jam proof, and can be co-located with other similar devices without suffering interference.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An apparatus for detecting a characteristic of objects within a field, comprising:

a transmitter which transmits a sequence of electro-magnetic signals in response to a transmit timing signal at a nominal pulse repetition frequency;

a receiver which samples echoes of the sequence of electro-magnetic signals from objects within the field with controlled timing, in response to a receive timing signal, and generates a sample signal in response to the samples, the sample signal indicating a characteristic of objects within the field; and a modulation circuit which imposes a modulation signal having the intermediate frequency on at least one of the transmitter signal amplitude, the transmit timing signal or the receive timing signal.

2. The apparatus of claim 1, wherein the modulation circuit includes:

a timing circuit which supplies the transmit timing signal to the transmitter and supplies the receive timing signal to the receiver, the relative timing of the transmit timing signal and the receive timing signal being modulated between a first relative delay and a second relative delay at an intermediate frequency, causing the receiver to sample the echoes such that time between transmission of signals in the sequence and sampling by the receiver is modulated at the intermediate frequency.

3. The apparatus of claim 2, wherein the electromagnetic signals in the sequence have a nominal pulse width, and the first relative delay and the second relative delay differ by less than the nominal pulse width.

4. The apparatus of claim 1, wherein the receiver includes an intermediate frequency stage comprising a synchronous detector synchronous with the intermediate frequency modulation.

5. The apparatus of claim 1, wherein the receiver includes an intermediate frequency stage comprising an automatic gain control circuit.

6. The apparatus of claim 1, wherein the receiver includes an intermediate frequency stage comprising:

a synchronous detector synchronous with the intermediate frequency modulation; and an automatic gain control circuit.

7. The apparatus of claim 1, wherein the receiver includes an intermediate frequency amplifier stage supplying an intermediate frequency receive signal, and a switch circuit having an input receiving the intermediate frequency receive signal, a first output and a second output, which synchronously switches the intermediate frequency receive signal to the first and second outputs synchronously with the intermediate frequency modulation.

8. The apparatus of claim 7, wherein the electromagnetic signals in the sequence have a nominal pulse width, and the modulation circuit includes:

a timing circuit which supplies the transmit timing signal to the transmitter and supplies the receive timing signal to the receiver, the relative timing of the transmit timing signal and the receive timing signal being modulated between a first relative delay and a second relative delay at an intermediate frequency, causing the receiver to sample the echoes such that time between transmission of signals in the sequence and sampling by the receiver is modulated at the intermediate frequency, and the first relative delay and the second relative delay differ by about one-quarter wavelength of a nominal center frequency of the electromagnetic signals, such that the first and second outputs of the switch circuit provide RF quadrature coding of the received echoes.

9. The apparatus of claim 1, wherein the modulation signal comprises a combination of the intermediate frequency and a second intermediate frequency.

10. The apparatus of claim 9, wherein the receiver includes:

an intermediate frequency stage comprising a first synchronous detector synchronous with the intermediate frequency modulation; and a second intermediate frequency stage comprising a second synchronous detector synchronous with the second intermediate frequency modulation.

11. The apparatus of claim 9, wherein the receiver includes an intermediate frequency stage comprising an automatic gain control circuit.

12. The apparatus of claim 9, wherein the receiver includes:

an intermediate frequency stage comprising an automatic gain control circuit, and a first synchronous detector synchronous with the intermediate frequency modulation; and a second intermediate frequency stage comprising a second synchronous detector synchronous with the second intermediate frequency modulation.

13. The apparatus of claim 9, wherein the receiver includes:

an intermediate frequency stage comprising an intermediate frequency noise limiter; and a second intermediate frequency stage comprising a statistical detector.

14. The apparatus of claim 1, wherein the modulation circuitry includes logic producing a coded signal, and is responsive to the coded signal to produce the modulation signal; and wherein the receiver includes an intermediate frequency stage comprising a synchronous detector synchronous with the coded intermediate frequency modulation.

15. An apparatus for detecting motion within a field, comprising:

a transmitter which transmits radio frequency signals in response to a transmit timing signal;

a receiver which samples echoes of the transmitted radio frequency signals from objects within the field with controlled timing, in response to a receive timing signal, and generates a sample signal in response to the samples;

a timing circuit which supplies the transmit timing signal to the transmitter and supplies the receive timing signal to the receiver, the timing circuit including a first circuit path coupled to the transmitter supplying the transmit timing signal and a second circuit path coupled to the receiver supplying the receive timing signal, one of the first and second circuit paths including modulation circuitry responsive to a modulation signal so that relative timing of the transmit timing signal and the receive timing signal is modulated between a first relative delay and a second relative delay; and a modulation control circuit which generates the modulation signal, the modulation signal having an intermediate frequency.

16. The apparatus of claim 15, wherein the receiver includes:

a sampler responsive to the receive timing signal which samples the echoes;

an intermediate frequency amplifier coupled to the sampler; and a synchronous detector, responsive to the modulation signal, for synchronously detecting intermediate frequency characteristics of the sampler output.

17. The apparatus of claim 16, wherein the sampler includes a charge holding capacitor which follows fluctuations in the sampled echoes at the intermediate frequency, and the intermediate frequency amplifier is coupled to the charge holding capacitor.

18. The apparatus of claim 17, wherein the intermediate frequency amplifier includes an automatic gain control circuit.

19. The apparatus of claim 15, wherein the receiver includes:

a sampler responsive to the receive timing signal which samples the echoes;

an intermediate frequency amplifier coupled to the sampler; and a switch circuit having an input coupled to the output of the intermediate frequency amplifier, a first output and a second output, which synchronously switches the output of the intermediate frequency amplifier to the first and second outputs in response to the modulation signal.

20. The apparatus of claim 19, wherein the radio frequency signals have a nominal center frequency, and the first relative delay and the second relative delay differ by about one-quarter wavelength of the nominal center frequency, such that the first and second outputs of the switch provide RF quadrature coding of the received echoes.

21. The apparatus of claim 15, wherein the modulation signal including a combination of the intermediate frequency and a second intermediate frequency, causing the receiver to sample the echoes such that time between transmission of signals in the sequence and sampling by the receiver is modulated at the intermediate frequency and at the second intermediate frequency.

22. The apparatus of claim 20, wherein the receiver includes:

a sampler responsive to the receive timing signal which samples the echoes;

an intermediate frequency amplifier coupled to the sampler; and a first synchronous detector, responsive to the intermediate frequency component of the modulation signal, for synchronously detecting intermediate frequency characteristics of the sampler output;

a second intermediate frequency amplifier coupled to the first synchronous detector; and a second synchronous detector responsive to the second intermediate frequency component of the modulation signal, for synchronously detecting second intermediate frequency characteristics of the sampler output.

23. The apparatus of claim 22, wherein the sampler includes a charge holding capacitor which follows fluctuations in the sampled echoes at the intermediate frequency, and the intermediate frequency amplifier is coupled to the charge holding capacitor.

24. The apparatus of claim 23, wherein the intermediate frequency amplifier includes an automatic gain control circuit.

25. A method for detecting motion in a field, comprising:

transmitting a sequence of RF signals with controlled timing;

sampling echoes of the transmitted sequence with controlled timing so that a range is defined by a round trip time-of-flight of the RF signals;

modulating at least one of the transmitting or sampling steps at an intermediate frequency; and amplifying the sampled echoes at the intermediate frequency, and synchronously detecting the amplified signal, synchronous with the modulating step.

26. The method of claim 25, wherein the step of modulating includes modulating the relative timing of the transmitting step and the sampling step between a first relative delay and a second relative delay at the intermediate frequency, so that the echoes are sampled such that time between transmission of signals in the sequence and sampling is modulated at the intermediate frequency.

27. The method of claim 26, wherein the difference between the first relative delay and the second relative delay is about one-quarter wavelength at the nominal center frequency of the signals in the sequence, and the synchronous detecting step includes demultiplexing the amplified intermediate frequency signal to produce in-phase and quadrature outputs.

28. The method of claim 25, including modulating at least one of the transmitting or sampling steps at a combination of the intermediate frequency and a second intermediate frequency.

29. The method of claim 28, wherein the amplifying step includes:

synchronously detecting the intermediate frequency component of the sampled echoes to produce an intermediate frequency signal; and synchronously detecting the second intermediate frequency component of the intermediate frequency signal to produce a base band signal.

30. The method of claim 28, wherein the amplifying step includes:

noise limiting the intermediate frequency component of the sampled echoes to produce an intermediate frequency signal; and statistically detecting the second intermediate frequency component of the intermediate frequency signal to produce a base band signal.

* * * * *